(12) United States Patent
Kulsrestha et al.

(10) Patent No.: US 6,355,835 B1
(45) Date of Patent: Mar. 12, 2002

(54) PROCESS FOR PREPARATION OF BENZENE DICARBOXYLIC ACIDS

(75) Inventors: Girendra Narain Kulsrestha, Dehradun; Mahendra Pratap Saxena, Uttar Pradesh; Ashok Kumar Gupta, Uttar Pradesh; Satish Kumar Sharma, Uttar Pradesh; Dinesh Prasad Bangwal, Uttar Pradesh; Hari Bhagwan Goyal, Uttar Pradesh; Rameshwar Prasad, Uttar Pradesh; Sanjib Mall, Maharashtra; Prakash D. Patel, Gujarat, all of (IN)

(73) Assignee: Chemintel (India) Private Limited, Gujarat (IN)

( * ) Notice: Subject to any disclaimer, the term of this patent is extended or adjusted under 35 U.S.C. 154(b) by 0 days.

(21) Appl. No.: 09/456,552

(22) Filed: Dec. 8, 1999

(51) Int. Cl.$^7$ .......................... C07C 51/16; C07C 51/255
(52) U.S. Cl. ....................................... 562/417; 562/412
(58) Field of Search .................................. 562/412, 417

(56) References Cited

U.S. PATENT DOCUMENTS 3,852,342 A * 12/1974 Hanotier et al.
5,591,890 A * 1/1997 Jacobson et al.

OTHER PUBLICATIONS

Aldrich Catalog Handbook of Fine Chemicals(1992–1993); pp. 1015, 745, and 1146.*

* cited by examiner

Primary Examiner—Paul J. Killos
Assistant Examiner—Farhad Forohar
(74) Attorney, Agent, or Firm—Dickinson Wright PLLC

(57) ABSTRACT

The present invention relates to a process for the preparation of benzene dicarboxylic acids by liquid phase oxidation of Xylene isomers using oxygen or air by oxidising in the presence of acetic acid as solvent, cobalt salt as catalyst and an initiator. The oxidation step is followed by flashing the said reaction mixture to remove volatile substances and cooling and filtering to get crude benzene di-carboxylic acid as a solid product and filtrate. The dicarboxylic acid solid product is recrystallised to get at least 99% pure benzene. The filtrate may be recycled.

6 Claims, 4 Drawing Sheets

Effect of cat/xy ratio

Effect of Pressure

Effect of Temperature

Effect of Initiator

PROCESS FOR PREPARATION OF BENZENE DICARBOXYLIC ACIDS

The present invention relates to a process for the preparation of benzene dicarboxylic acids by liquid phase oxidation of Xylene isomers using oxygen or air.

The main embodiment of the process for the preparation of specific benzene-dicarboxylic acid, namely phthalic acid, terephthalic acid, or isophthalic acid resides in the oxidation of corresponding xylene isomer in liquid phase using oxygen or air. The impurity of carboxy-benzaldehyde is almost eliminated in the product thus formed.

BACKGROUND OF THE INVENTION

Benzene dicarboxylic acids are industrially prepared by oxidation of the corresponding xylene isomers. While phthalic acid can be produced by vapour phase as well as liquid phase air oxidation of o-xylene, terephthalic acid and isophthalic acid can be produced by liquid phase processes only. This is mainly die to the reason for conversion of xylene and selectivity to corresponding phthalic acids being considerably lower in the vapour phase oxidation.

The production of terephthalic acid as known conventionally uses cobalt acetate as catalyst and aldehydes or ketones as catalyst-activators to provide free radicals in the system that help in the oxidation. The activator is usually used in proportions similar to the catalyst. Due to high quantities of activator and catalyst used in these processes, acetic acid is produced as a by-product. It has been observed that the consumption of initiator in the conventional process is relatively high. The procedure to purify phthalic acid has been found to be energy intensive and elaborate, where, in the first step filtered terephthalic acid is first leached with acetic acid in a soaking chamber at high temperature for a time sufficient for dissolving the impurities formed as intermediates of the reaction and the catalyst in the acetic acid. The mixture is then cooled and sent to a final purification stage. Subsequently the solid terephthalic acid is sublimed and given a catalytic treatment to remove traces of organics and metals. The consumption of large quantities of activator used in the process and high energy as well as time consuming separation and purification steps are main drawbacks of this conventional process.

In an another conventionally known process for the preparation of terephthalic acid, a bromide promoted cobalt and manganese catalyst is used in the presence of air as oxidant. However, this process does not provide the desired results, as it has high concentration of carboxybenzaldehyde impurity.

U.S. Pat. No. 5,132,480 (1992) teaches a process for the production of highly pure isophthalic acid in the presence of Cobalt Manganese Bromide catalyst in liquid phase using acetic acid as solvent at a temperature between 180° C. to 210° C. in two steps, where in the first step the concentration of 3-Carboxybenzaldehyde is obtained to be 10,000 PPM which is reduced to 100 PPM or lower than 100 PPM in the second step.

U.S. Pat. No. 5,189,209 (1992) claims a process for the production of highly pure isophthalic acid by liquid phase hydrogenation of crude Iso-phthalic acid in aqueous acetic acid in the presence of a noble metal catalyst of Group VIII using water in the range of 1 to 50% by weight at a temperature in the range 170° C. to 300° C. and pressure between 15 to 50 kg/cm$^2$.

U.S. Pat. No. 5,371,283 (1994) describes a process for the production of terephthalic acid. Oxygen or an oxygen-rich gas is used in the presence of acetic acid in a reaction system that mitigates the flammability hazards associated therewith. This process basically describes the use of a particular type of reactor for terephthalic acid production.

U.S. Pat. No. 5,770,765 (1998) describes a process for producing high-purity isophthalic acid by subjecting the mother liquor obtained from oxidation reaction of m-xylene to series of hydrogenation and oxidation steps using water as solvent for the dissolution of isophthalic acid obtained by crystallizing the oxidation solution. The aqueous solution is subjected to catalytic hydrogenation and oxidation to reduce intermediate-impurities. The invention, thus disclosed in the patent requires an additional reaction steps to reduce impurities in isophthalic acid.

U.S. Pat. No. 3,974,214, (1976) discloses a process for the preparation of isophthalic acid cobalt catalyst wherein the formation of color imparting compounds like the meta toluic acid are reduced in the final product. This is achieved by carrying out the reaction in two reactors and adjusting the concentration of the initiator and the catalyst between the reactors. The ratio of isophthalic acid and the meta toluic acid between the reactors is carefully manipulated to achieve the desired result of less than 0.4% MTA in the final product. In this process between the first and second stages of the reactors a lot of activator is added (of proportions equal to that of MTA at the end of first stage). It has been claimed that by targeting the oxidation of MTA in the middle of the reaction rather than wait till all isophthalic acid is formed, the amount of color imparting bodies occluding in isophthalic acid are reduced.

In summary, hitherto the xylene oxidation processes have generally employed bromide promoted cobalt-manganese catalysts. In other versions of such processes, cobalt-manganese catalyst promoted by a free-radical-producing compound like acetaldehyde and 2-butanone and the like are used.

All the above referenced processes suffer from certain disadvantages as the use of bromide promoter leads to equipment corrosion. Since the process operates under severe conditions of high pressure and temperature, the equipment corrosion is a risk to safety besides the high cost of the corrosion resistant material needed for construction.

Further, the use of molecular proportions of organic promoters leads to the simultaneous and inadvertent production of acetic acid as a by-product, which is uneconomical as the promoters are expensive raw material for acetic acid production. The di-carboxylic acid product contains carboxybenzaldehyde as a by-product which is very difficult to be separated and thus makes the product unsuitable for use as a monomer. Moreover, product purification involves a selective hydrogenation or oxidation of the impurity and adds to the cost of production.

Hence, a process which does not use corrosive bromine compounds as catalyst ensures the complete conversion of the intermediates like the Carboxy-benzaldehyde and Meta-toluic acid in the oxidation reactor and achieves low concentrations of these compounds in the final product thus is having a great economic potential.

The objective of the present invention is to provide an improved process wherein the reactivity of carboxybenzaldehyde by-product is enhanced by use of a suitable concentration of a cobalt catalyst and process conditions without adversely effecting the conversion of xylene and selectivity to the benzene dicarboxylic acid product. The carboxybenzaldehyde impurity in the product is therefore almost eliminated in this process, thereby eliminating the requirement of another purification process step downstream of the reactor. The catalyst activator is used in very small quantities compared to the conventional processes. Further, use of bromine catalyst is avoided.

The present invention relates to a process for the preparation of benzene-dicarboxylic acid, wherein catalyst does not contain bromide promoters or organic promoter in molecular proportions.

The subject process comprises the use of substantial proportion of a cobaltous salt from 5.0 to 25 mole percent of xylene feed as the catalyst. The acid component of the salt is chosen from acetate, propionate, butyrate or phthalates, isophthalate, terephthalate and the like. The initiator is used in the substantially reduced quantity as compared to the quantity of the initiators used in the conventional processes and is selected from acetaldehyde, tolualdehyde or ketones such as butanone, methyl ethyl ketone etc. in proportions of 0.01 to 1 mole per mole of the metal salt mixture used as the catalyst. The specific xylene isomer is oxidized with air or oxygen at a pressure of 5 to 80 $kg/cm^2$ and temperature of 100° C. to 130° C. in the presence of acetic acid solvent for a period ranging between one hour and six hours. The solvent to xylene weight ratio is ranged between 4 to 20. The said reaction mixture is then flashed to room temperature and pressure to remove volatiles like water and unreacted Xylene and some other compounds, which is followed by cooling to 20° C.–40° C. and filtering off or centrifuging out the crystallized crude product. The crude benzene dicarboxylic acid product is at least 97% pure with only traces of carboxybenzaldehyde. The product is purified to at least 99% by re-crystallization from a suitable solvent like methanol, ethanol, water, acetic acid and the like. The dehydrated filtrate containing the solvent, catalyst and intermediates is re-cycled after adding make-up amounts of catalyst, solvent and the initiator.

The reaction is carried out in a 300 ml autoclave made of stainless steel provided with a mechanical stirrer, a gas delivery tube, a reflux condenser, a thermometer pocket and a rupture disc. The autoclave is electrically heated and has internal cooling coils. The system operates as a batch reactor. The exit gases passes through an ice cooled trap and then bubbled through cold (−20° C.) toluene to trap any carryover m-xylene.

The conversion of xylene is nearly total (98–100%) and the selectivity on recycle basis to dicarboxylic acid achieved is more than 98% based on xylene reacted. The carboxybenzeldehyde as impurity in the product is eliminated or reduced considerably.

A series of experiments were conducted to establish the effect of various parameters on the oxidation of xylenes. The effect of some of the relevant parameters are shown with reference to the accompanying drawings, wherein:

FIG. 1, is a graph exhibiting the effect of catalyst to xylene ratio on conversion and selectivity. As evident, until molar ratio 0.1 selectivity and conversion increases as the ratio of catalyst to xylene is increased while beyond molar ratio 0.1 there is no effect on the conversion and selectivity. Therefore, the optimum catalyst loading used is 0.1 moles per mole of xylene charged. At these concentrations of the catalyst the mechanism of the reaction is electron-transfer as opposed to others where Co-Mn-Br catalyst system is employed, which have free-radical mechanism leading to increased concentrations of carboxybenzaldehyde in the final product necessitating an expensive hydrogenation step for the purification of the di-acid product formed. This step has been avoided completely in the subject process by selecting the desired proportion of the catalyst so that oxidation takes place that ensures complete conversion of the intermediates to the desired product.

Figure 1:
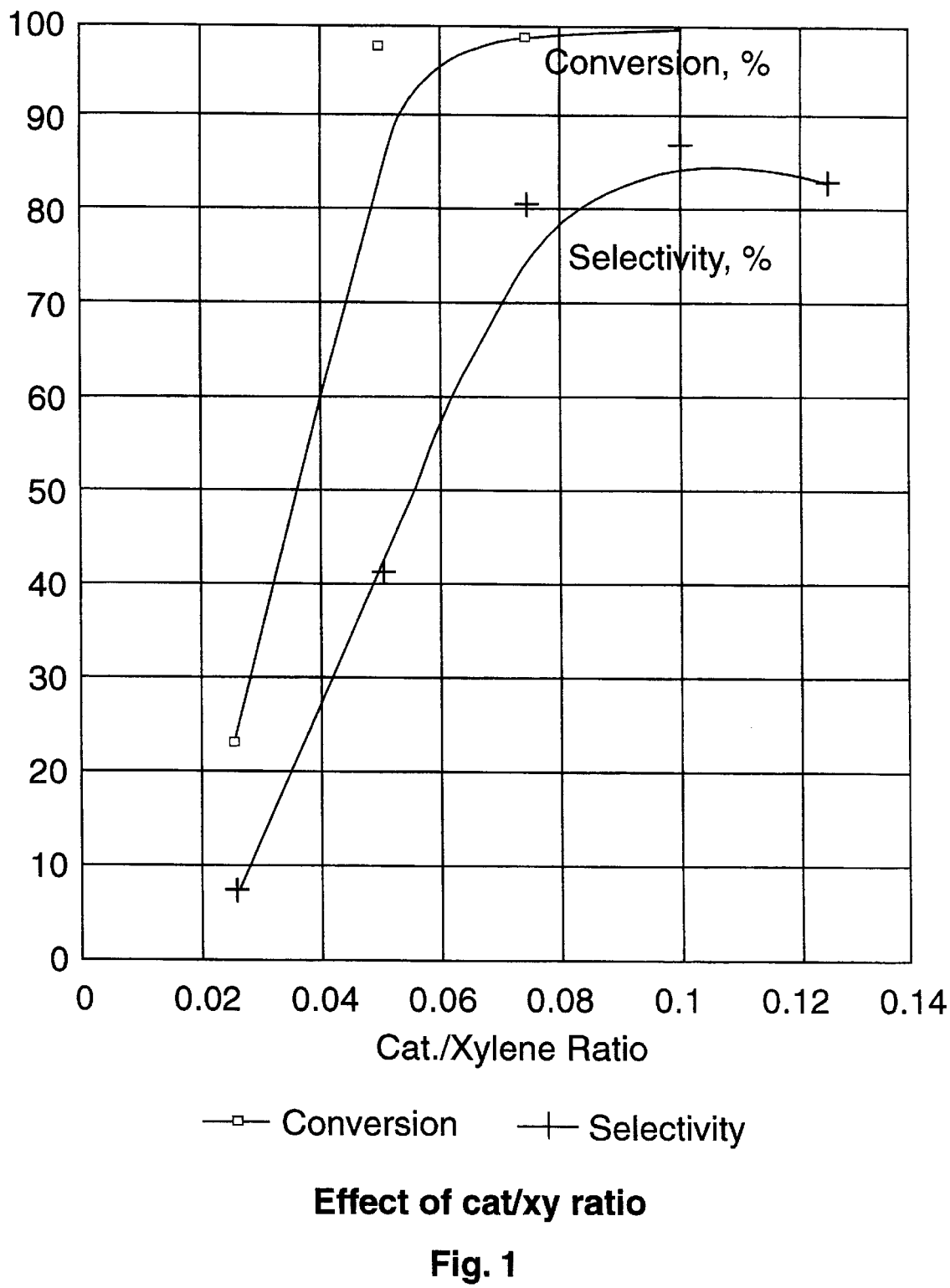
Figure 2:
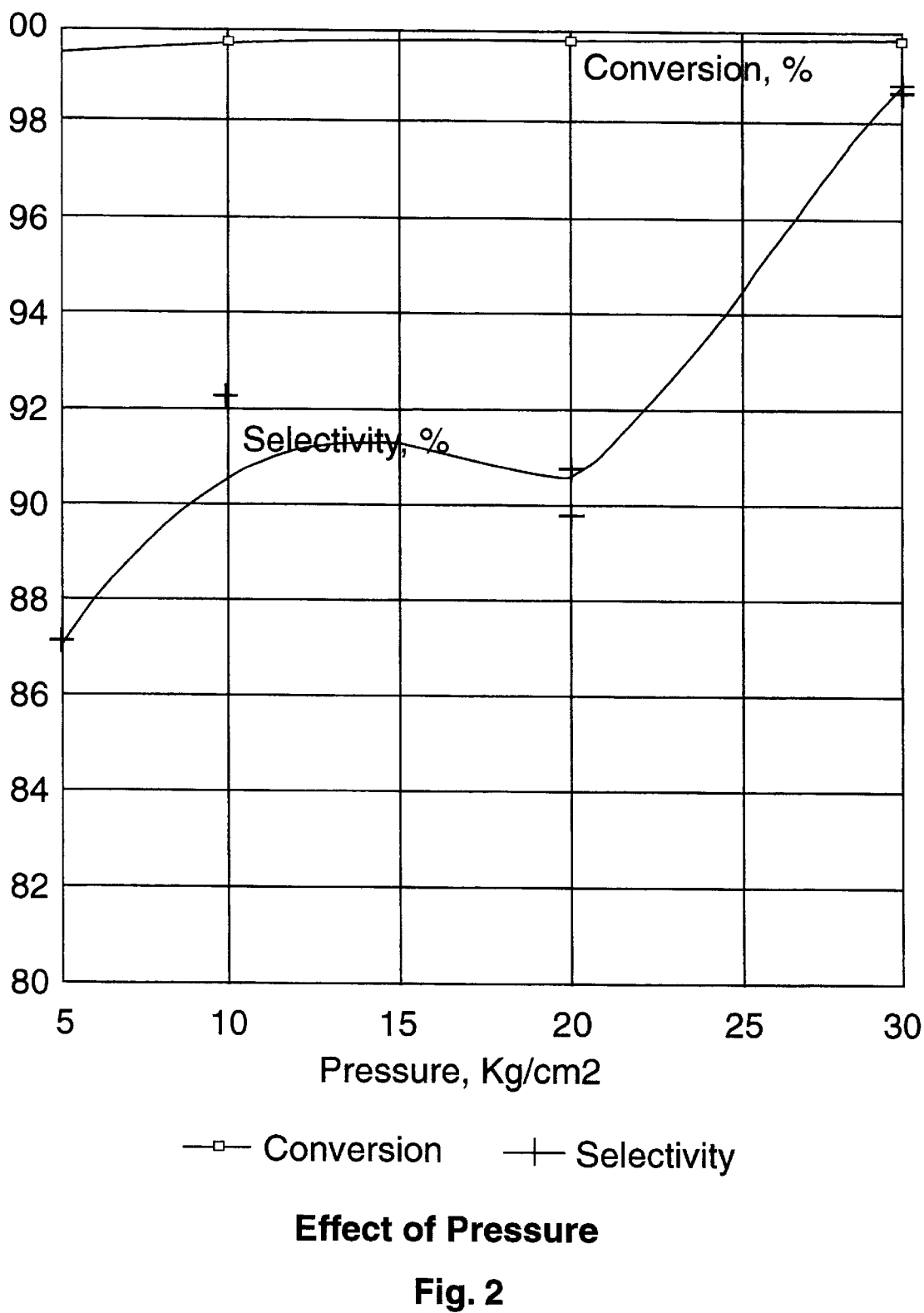
FIG. 2 shows a graph exhibiting the conversion of m-xylene and selectivity to isophthalic acid at the prescribed pressure of the subject process.
Figure 3:
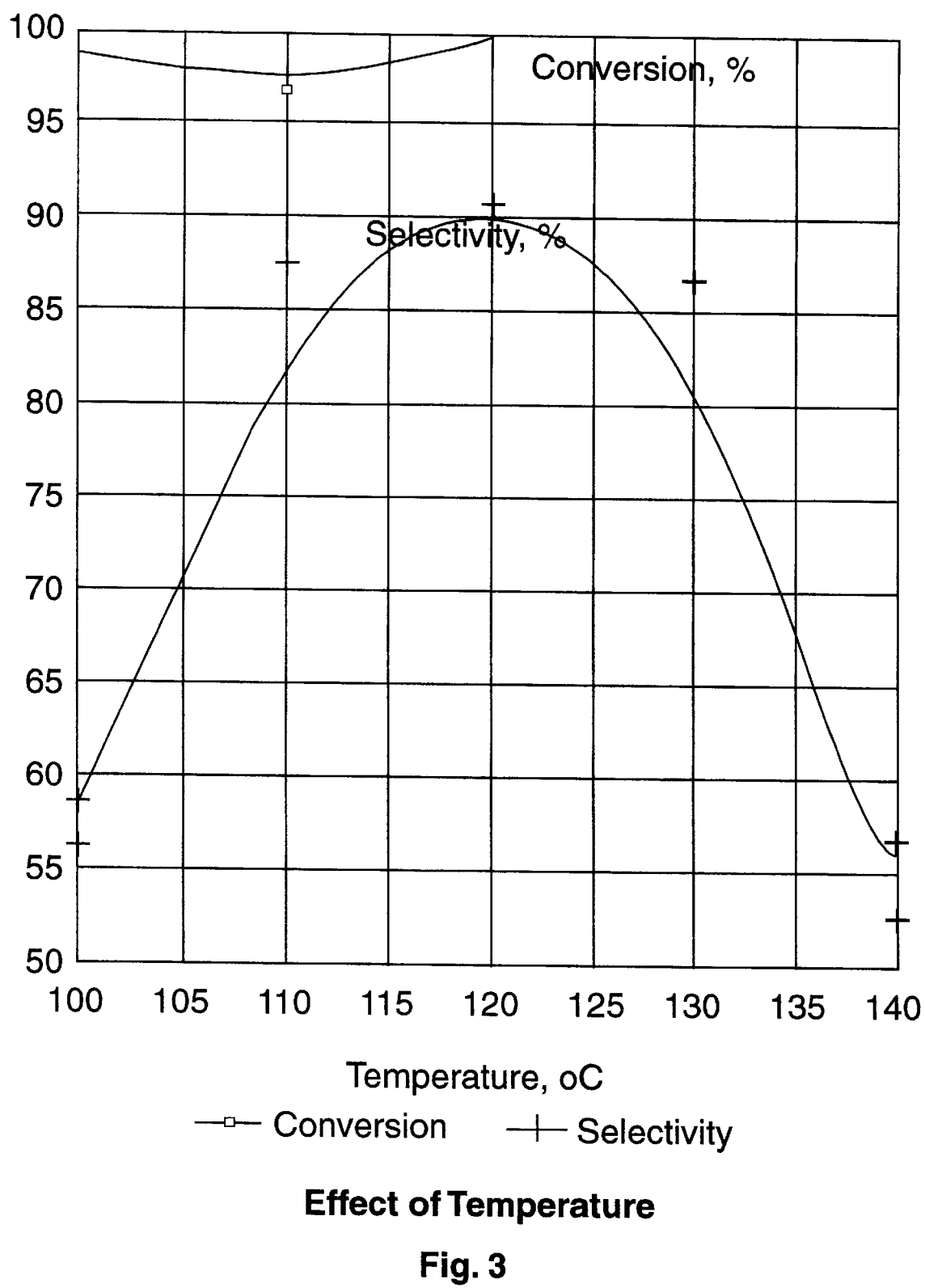
FIG. 3 shows a graph exhibiting the effect of temperature on conversion of m-xylene and selectivity to isophthalic acid. Even though the conversion is 100% above 110° C., the selectivity to adipic acid falls sharply beyond 120° C. due to deactivation of the cobalt catalyst beyond this temperature.
Figure 4:
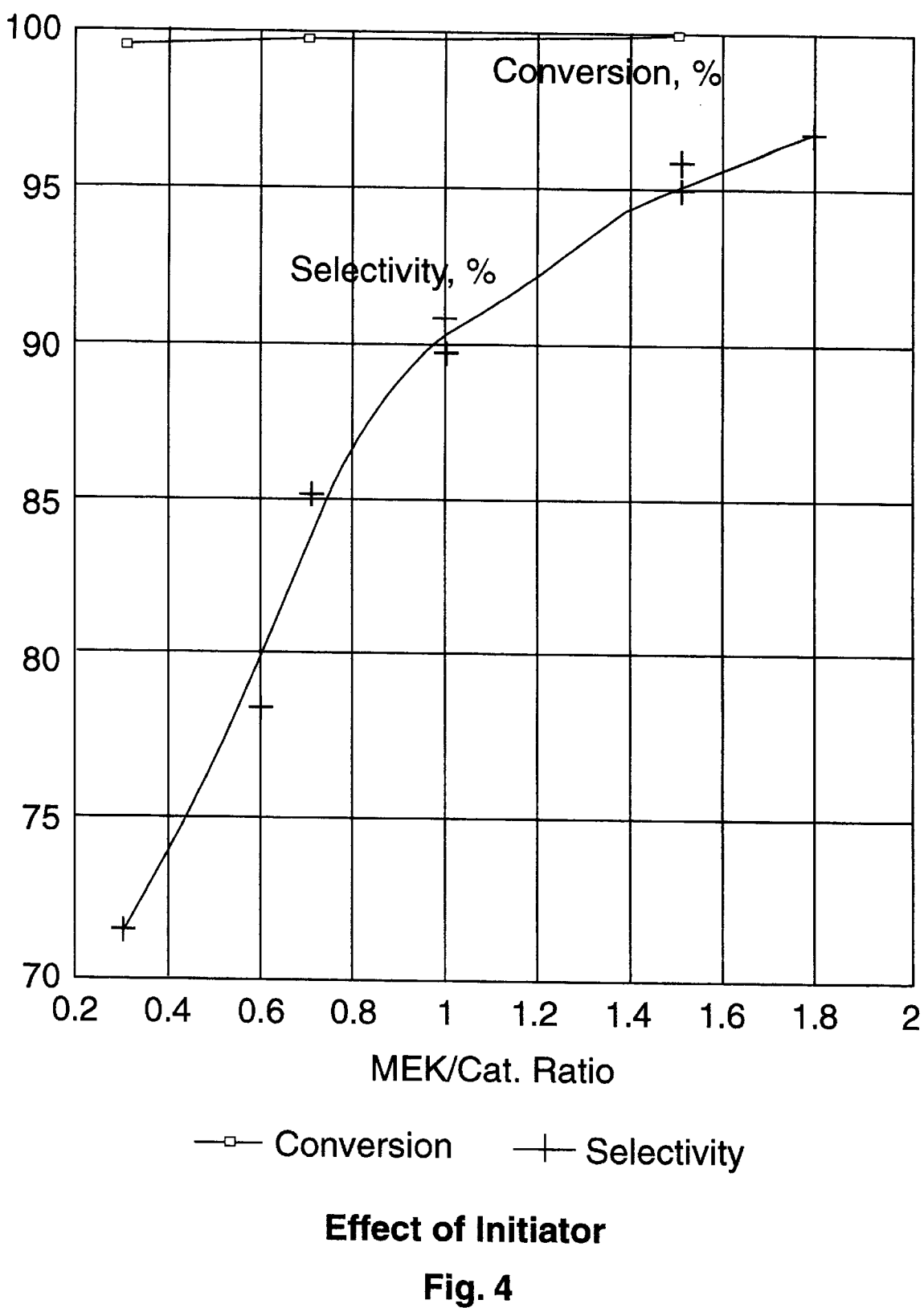

FIG. 4 shows a graph exhibiting the effect of initiator/Catalyst ratio on the conversion of m-xylene and selectivity to isophthalic acid. It has been found that the conversion is essentially complete with even low concentrations of the initiator. But selectivity increases with the initiator concentration. At an initiator/catalyst ratio of 1.0 actual is calculated as 0.05 Kg of specific phthalic acid produced, which is much lower than the amount of initiator used in the available conventional process.

Accordingly, the subject invention relates to a process for the preparation of benzene-dicarboxylic acid by liquid phase oxidation of xylene isomer which comprises:

oxidizing a xylene isomer with air or oxygen in an autoclave at a pressure of 5–80 $kg/cm^2$ and temperature ranging between 100–150° C. in the presence of an acetic acid solvent, a cobalt salt catalyst in the ratio of 5.0 to 25 mole percent of said xylene feed and an initiator in proportions of 0.05 to 1 mole per mole of the said catalyst, for a period of 1 to 6 hours to form a reaction mixture;

flashing the said reaction mixture to remove volatile substances, followed by cooling to 20–40 C.° and filtering/centrifuging to get crude benzene dicarboxylic acid as solid product and filtrate;

recrystallizing the said crude benzene dicarboxylic acid to get at least 99% pure benzene dicarboxylic acid; in the presence of a solvent selected from methanol, ethanol, water or acetic acid.

Further, the present invention defines a process for the preparation of benzene-dicarboxylic acid by liquid phase oxidation of xylene isomer which comprises:

oxidizing a xylene isomer with air or oxygen in an autoclave at a pressure of 5–80 $kg/cm^2$ and temperature ranging between 100–150° C. in the presence of an acetic acid solvent, a cobalt salt catalyst in the ratio of 5.0 to 25 mole percent of said xylene feed and an initiator in proportions of 0.05 to 1 mole per mole of the said catalyst, for a period of 1 to 6 hours to form a reaction mixture;

flashing the said reaction mixture to remove volatile substances, followed by cooling to 20–40 C.° and filtering/centrifuging to get crude benzene dicarboxylic acid as solid product and filtrate;

recrystallizing the said crude benzene dicarboxylic acid to get at least 99% pure benzene dicarboxylic acid; in the presence of a solvent selected from methanol, ethanol, water or acetic acid and re-cycling the filtrate with less than 1% water and containing said solvent, said catalyst and said intermediates as well as organics and unreacted xylene.

The invention is described in the following examples by way of illustrations only and should not be construed to limit the scope of the invention.

EXAMPLES

Example 1

21.2 g m-Xylene, 150 g glacial acetic acid, 5.0 g cobaltous acetate and 1.2 g 2-butanone were charged into a 300 CC stirred stainless steel autoclave. 100 CC/min. Oxygen was bubbled through the sparger tube and the mixture was oxidized at 125° C. at 35 kg/cm² pressure. Sparging 100 cc of O² per minute through the contents for four hours after which the reaction mixture was allowed to flash to 35° C. at 1 atm. pressure, cooled and then centrifuged. The solid crude product obtained was 29.1 g and contained 98.5% isophthalic acid, 1.4% m-toluic acid and only about 100 PPM, 3-carboxybenzaldehyde. The filtrate containing 3.6 g organic product consisting of 80.3% m-toluic acid, 12.5% isophthalic acid and 7.2% unidentified components is recycled. The crude product on crystallization from water yielded 28.5 g, 99.9% Isophthalic acid with less than 15 PPM 3-carboxybenzaldehyde.

Example 2

21.2 g m-Xylene, 160 g glacial acetic acid, 4.0 g cobaltous acetate and 0.5 g paraldehyde were treated with oxygen, 150 cc/min, in an autoclave at 130° C., 30 kg/cm² for 3 hours. The reaction mixture was flashed to 35° C. at 1 atm. pressure, cooled and then filtered. The solid product obtained, 28.8 g, contained 98.3% Isophthalic acid, 1.6% m-toluic acid and only about 120 PPM, 3-carboxybenzaldehyde. On re-crystallization, the product purity was 99.9%, with less than 15 PPM 3-carboxybenzaldehyde. The filtrate contained 4.5 g organic product consisting of 84.5% m-toluic acid, 12.3% Isophthalic acid and 3.2% unidentified components.

Example 3

A mixture of 21.2 g p-Xylene, 200 g glacial acetic acid, 6.0 g cobaltous acetate and 0.4 g 2-butanone treated with oxygen (100 cc per minute) using a sparger tube in an autoclave at 120° C., 20 kg/cm² for four hours. The reaction mixture was flashed to 25° C. at one atm. pressure, cooled and filtered. The yield of crude (98.6%) terephthalic acid was 30.2 g. The filtrate containing 4.5 g organic product consisting of 15.29% terephthalic acid, 75.8% toluic acid and 9.0% unidentified components is recycled. The crude product on crystallization yield terephthalic acid of 99.9% purity with less than 15 PPM 4-carboxybenzaldehyde.

Example 4

A mixture of 21.2 g m-Xylene, 200 g glacial acetic acid, 5.2 g cobaltous acetate and 1.0 g 2-butanone was oxidized with air (500 cc per minute) in an autoclave lifted with gas sparger at 130° C., 40 kg/cm² for five hours. The reaction mixture was filtered to yield 30.1 g. crude 98.1% Isophthalic acid. The filtrate along with 21.2 g m-Xylene, 0.25 g make up cobaltous acetate, and 0.4 g 2-butanone was oxidized with 500 cc per minute air at 130° C., 40 kg/cm² for five hours. The reaction mixture on filtration at 350 cc yielded 32.5 g crude (98.5) Isophthalic acid. This on recrystallization from water yielded 31.5 g, 99.9% pure isophthalic acid. The product contained less than 15 PPM 3-carboxybenzaldehyde.

Thus, the subject process for the production of benzene dicarboxylic acid involves liquid phase oxidation of xylenes in the presence of solvent which uses cobalt catalyst with very low concentrations of activator. There are no corrosive initiators/activators like bromine based compounds. The catalyst concentration is chosen such that under the reaction conditions, the oxidation takes place via an electron transfer route. This helps converting the intermediates like toluic acid and carboxybenzaldehyde to phthalic acid very fast, thereby reducing the concentration of these compounds in the final product formed. Thus purification of the phthalic acid is easy, does not involve hydrogenation or any other energy intensive steps but involves recrystallisation from water or any suitable solvent.

The subject invention is merely a statement of invention and should not in any way construed to restrict the scope of the invention.

We claim:

1. A process for the preparation of benzene-dicarboxylic acid by liquid phase oxidation of xylene isomer comprising:

oxidizing a xylene isomer with air or oxygen in an autoclave at a pressure of 5–80 kg/cm² and temperature ranging between 100–150° C. in the presence of an acetic acid solvent, a cobalt salt catalyst in the ratio of 5.0 to 25 mole percent of said xylene feed and an initiator in proportions of 0.05 to 1 mole per mole of the said catalyst, for a period of 1 to 6 hours to form a reaction mixture;

flashing the said reaction mixture to remove volatile substances, followed by cooling to 20–40 C.° and filtering/centrifuging to get crude benzene dicarboxylic acid as solid product and filtrate;

recrystallizing the said crude benzene dicarboxylic acid to get at least 99% pure benzene dicarboxylic acid; in the presence of a solvent selected from methanol, ethanol, water or acetic acid.

2. A process for the preparation of benzene-dicarboxylic acid by liquid phase oxidation of xylene isomer comprising:

oxidizing a xylene isomer with air or oxygen in an autoclave at a pressure of 5–80 kg/cm² and temperature ranging between 100–150° C. in the presence of an acetic acid solvent, a cobalt salt catalyst in the ratio of 5.0 to 25 mole percent of said xylene feed and an initiator in proportions of 0.05 to 1 mole per mole of the said catalyst, for a period of 1 to 6 hours to form a reaction mixture;

flashing the said reaction mixture to remove volatile substances, followed by cooling to 20–40 C.° and filtering/centrifuging to get crude benzene dicarboxylic acid as solid product and filtrate;

recrystallizing the said crude benzene dicarboxylic acid to get at least 99% pure benzene dicarboxylic acid; in the presence of a solvent selected from methanol, ethanol, water or acetic acid and re-cycling the said filtrate with less than 1% water and containing said solvent, said catalyst and said intermediates as well as organics and unreacted xylene.

3. A process as claimed in claim 1, wherein the acid component of the said cobaltous salt is selected from acetate, propionate, butyrate or phthalates, isophthalates or tererphthalates.

4. A process as claimed in claim 1, wherein the said initiator is selected from acetaldehyde, tolualdehyde or methyl ethyl ketone in proportions from 0.05 to 1.0 mole per mole of the metal salt mixture used as the catalyst.

5. A process as claimed in claim 2, wherein the acid component of the said cobaltous salt is selected from acetate, propionate, butyrate or phthalates, isophthalaetes or terephthalates and the like.

6. A process as claimed in claim 2, wherein the said initiator is selected from acetaldehyde, tolualdehyde or ketones such as butanone, methyl ethyl ketone in proportions of 0.05 to 1 mole per mole of the metal salt mixture used as the catalyst.

* * * * *